Figure 1:
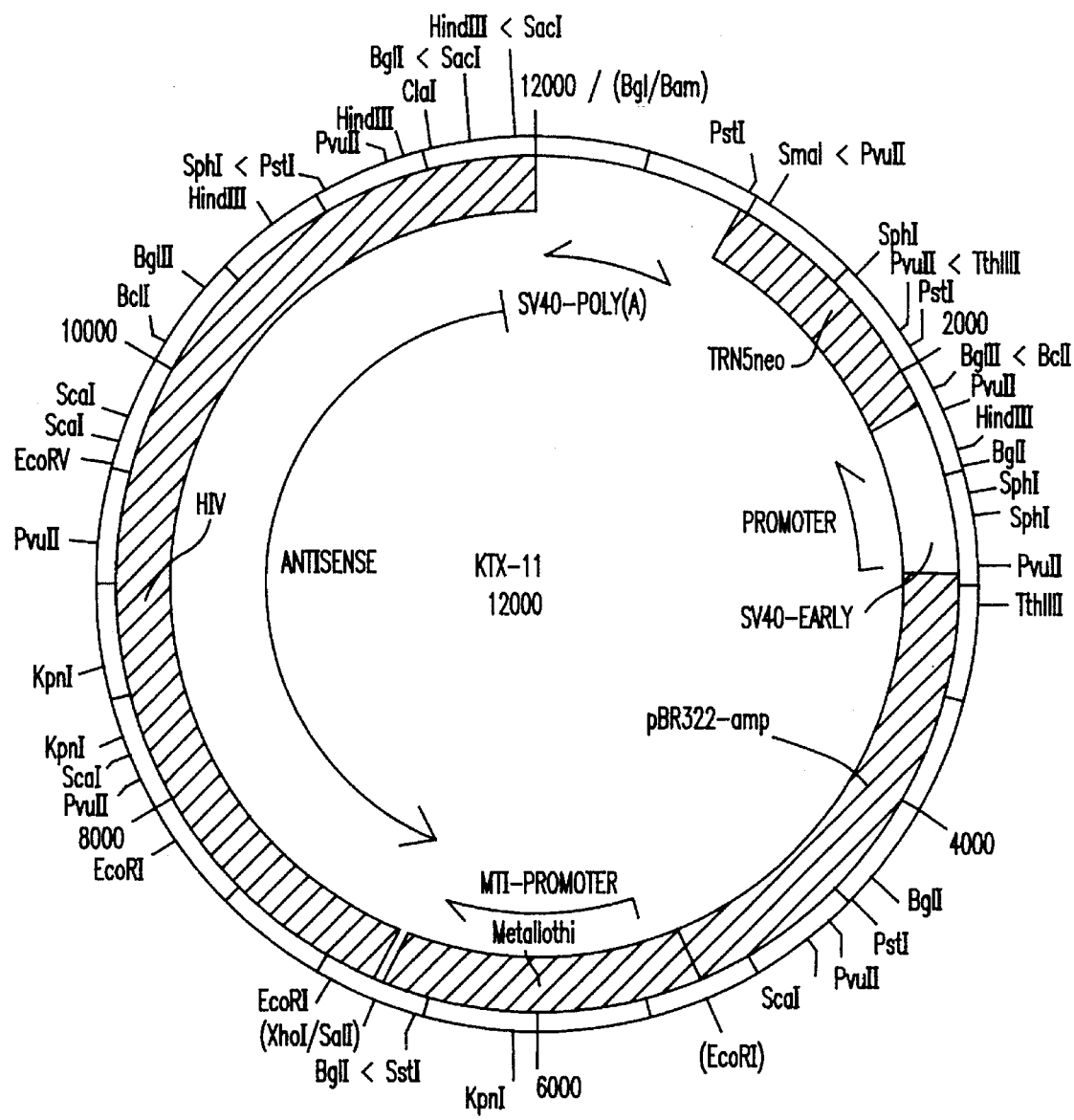

United States Patent [19]

Kretschmer et al.

[11] Patent Number: 5,583,035
[45] Date of Patent: Dec. 10, 1996

[54] HIV ANTISENSE EXPRESSION VECTORS

[75] Inventors: Axel Kretschmer; Horst-Peter Antonicek, both of Begisch Gladbach; Jörg Baumgarten; Antonius Loebberding, both of Wuppertal; Burkhard Mielke, Leverkusen; Wolfgang Springer, Wuppertal; Udo Stropp, Haan, all of Germany; Mark-Michael Struck, Bern, Switzerland; Lothar Biesert, Frankfurt, Germany; Helga Rübsamen-Waigmann, Bad Soden, Germany; Hary Suhartono, Frankfurt, Germany; Thomas-Peter Hausner, Cologne, Germany

[73] Assignee: Bayer Aktiengesellschaft, Leverkusen, Germany

[21] Appl. No.: 338,355

[22] Filed: Nov. 14, 1994

Related U.S. Application Data

[63] Continuation of Ser. No. 987,506, Dec. 7, 1992, abandoned.

[51] Int. Cl.⁶ .............................. C12H 5/22; C12H 15/85
[52] U.S. Cl. ................. 435/240.2; 435/6; 435/91.1; 435/91.21; 435/91.33; 435/172.3; 435/320.1; 536/23.1; 536/23.72; 536/24.5
[58] Field of Search ..................... 514/44; 536/23.1, 536/23.72, 24.5; 435/240.2, 320.1, 172.3, 6, 91.1, 91.21, 91.33

[56] References Cited

FOREIGN PATENT DOCUMENTS

| 303292 | 2/1989 | European Pat. Off. . |
| 0331939 | 9/1989 | European Pat. Off. . |
| 351585 | 1/1990 | European Pat. Off. . |
| 4126484 | 2/1993 | Germany . |
| 88/10311 | 12/1988 | WIPO . |
| 9013641 | 11/1990 | WIPO . |
| 9215680 | 9/1992 | WIPO . |
| 92/17211 | 10/1992 | WIPO . |

OTHER PUBLICATIONS

J. A. Levy, 1993, Microbiol. Rev., 57: 183–289.
S. Kyoizumi et al., 1992, Blood, 79: 1704–1711.
S. E. Moiser et al., 1993, Science, 260: 689–692.
Wain–Holsson et al. Cell 40: 9–17, 1985.
Gallo et al. Nature 333:504, 1988.
Vanturelli et al. PNAS 87:5963 (1990).
Wu et al. Oucogen 5:873 (1990) Biosis #90052682.
Colomer et al. Proc. Am. Ass. Car. Res. Ann. Meet. 31:308 (1990) Provided as Biosis #39042938.
Nitta et al. Neurol. Surg. 20: 857 (1992) Biosis #95006 447.
McManaway et al. Lancet 07 Apr. 1990 335:808.
Caaceislo et al. Science 245:1107 (1989).
Amini et al. Mol. Cell. Biol. Jul. 1986:2305.
Anderson et al. Mol. Immunol. 26:985 (1989).
Boyd, M. et al. AIDS 5(2): 225–226 (1991).

Nishikura, K. et al. Mol. Cell. Biol. 7(2): 639–649 (1987).
Markham, B. E. et al. J. Biol. Chem. 265(11): 6489–6493 (1990).
Holt, J. T. et al. Proc. Natl. Acad. Sci. 83: 4794–4798 (1986).
Rhodes, A. et al. J. Gen Virol. 71:1965–74 (1990).
Freie, S. M. et al. Proc. Natl. Acad. Sci. 83:9373–9377 (1986).
Koutoh, K. et al. Cell Str. Function 12(6):575–80 (1987) (Abstract attached).
Noley, S. et al. Immunobiol 184: 193–207 (1992).
Sczakiel, G. et al. J. Virol. 65(1):468–472 (1991).
Gyotoku, J. et al. Virus Genes 5(3):189–202 (1991).
Biochemical and Biophysical Research Communications, vol. 169, No. 2, 15 Jun. 1990, Duluth, Minnesota, pp. 643–651.
Journal of Biological Chemistry, vol. 265, No. 27, 25 Sep. 1990, Baltimore, MD, pp. 16337–16342.
K. W. Culver et al., Transplant. Proceed., 23: 170 (1991).
Title page, UWGCG printout VI:HIVHXB2CG (1988).
L. Ratner et al., Nature, 313: 277 (1985).
S. Wain–Hobson et al., Cell, 40: 9 (1985).
V. W. van Beusecheme t al., PNAS, 89: 7640 (1992).
W. F. Anderson, Science, 256: 808 (1992).
A. D. Miller, Nature, 357: 455 (1992).
J. L. Fox, Bio/Technology, 11: 780 (1993).
J. L. Fox, Bio/Technology, 11: 1227 (1993).
L. Han et al., PNAS, 88: 4313 (1991).
P. H. Correll et al., Blood, 80: 331 (1992).
T. Ohashi et al., PNAS, 89: 11332 (1992).
M. Bregni et al., Blood, 80: 1418 (1992).
H, Weinthal et al., Bone Marrow Transplantation, 8: 403 (1991).
K. Rittner et al., Nuc. Acids Res. 19, 1421 (1991).
K. M. Takayama und M. Inouye, Critital Reviews in Biochemistry and Molecular Biology 25, 155 (1990).
J. Mol et al., FEBS Letters 268, 427 (1990).
T. Bunch und L. Goldstein, Nucleic Acids Research 17, 9761 (1989).
M. Cuozzo et al., Biotechnology 6, 549 (1988).
T. Ruden und E. Gilboa, J. Virol. 63, 677 (1989).
R. Dulbecco in Virology, 2. Ed., p. 355; Publisher: J. B. Lippincott Company, Philadelphia (1988).
G. Sczakiel et al., Biochem. Biphys. Res. Com. 169 (1990).
O. I. Mirosknichenko et al., Gene 84, 83 (1989).
W. A. Haseltine et al., Scientific American USA, 1988, 34–42.
N. Glanville et al., Nature 292, 267–269 (1982).
S. Y. Kao et al., 330, 489 (1987).
Wigler et al., 1977, Cell 11, 223.

(List continued on next page.)

*Primary Examiner*—John L. LeGuyader
*Attorney, Agent, or Firm*—Sprung Horn Kramer & Woods

[57] ABSTRACT

The present invention relates to the targeted blocking of the genetic information of the viral messenger ribonucleic acid (mRNA) for virus replication (e.g. of HIV) in transfected, haematopoietic cells with particularly suitable expression systems, which express a complementary "antisense RNA".

4 Claims, 13 Drawing Sheets

OTHER PUBLICATIONS

L. G. Davis et al., Basic Methods in Molecular Biology, Elsevier, New York, (1986).

PCR Technology Principles and Application for DNA Amplification, Ed. Henry A. Erlich, M. Stockton Press, New York (1989).

G. J. Graham et al., PNAS 87, 5817 (1990).

R.Y–L. To et al, in Gene Regulation, 261 pp. (1992).

T. Shimida et al., Antiviral Chem. & Chemotherapy 2, 133 (1991).

G. Sczakiel et al., J. Virol. 66, 5576 (1992).

H. Kuhnel et al., Nucleic Acids Research, 18, 6142 (1990).

European J. Biochem. 154, 581–586 (1986).

Proc. Natl. Acad. Sci. 82, 2652–2656 (1985).

Cell 41, 497–508 (1985).

Proc. Natl. Acad. Sci. 80, 21–25 (1983).

Proc. Natl. Acad. Sci. 79, 7410–7414 (1982).

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
    ( A ) LENGTH: 17 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO: 1:

CAAACCCTTT GCGCCCG                                            17

( 2 ) INFORMATION FOR SEQ ID NO: 2:

( i ) SEQUENCE CHARACTERISTICS:
    ( A ) LENGTH: 17 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO: 2:

ACTCGTCCAA CGACTAT                                            17

( 2 ) INFORMATION FOR SEQ ID NO: 3:

( i ) SEQUENCE CHARACTERISTICS:
    ( A ) LENGTH: 21 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO: 3:

TTTTTTCACT GCATTCTACT T                                       21

( 2 ) INFORMATION FOR SEQ ID NO: 4:

( i ) SEQUENCE CHARACTERISTICS:
    ( A ) LENGTH: 25 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO: 4:

CTTTCCAAAA TGTCGTAACA ACTCC                                   25

( 2 ) INFORMATION FOR SEQ ID NO: 5:

( i ) SEQUENCE CHARACTERISTICS:
    ( A ) LENGTH: 21 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO: 5:

ATTTAGGTGA CACTATAGAA T                                       21

( 2 ) INFORMATION FOR SEQ ID NO: 6:

( i ) SEQUENCE CHARACTERISTICS:
    ( A ) LENGTH: 18 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO: 6:

ATGGAGCCAG TAGATCCT          18

( 2 ) INFORMATION FOR SEQ ID NO: 7:

( i ) SEQUENCE CHARACTERISTICS:
        ( A ) LENGTH: 13 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 7:

TCTACCATGT CAT          13

( 2 ) INFORMATION FOR SEQ ID NO: 8:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 8:

TCTGTTCTAC CATGTCAT          18

HIV ANTISENSE EXPRESSION VECTORS

This application is a continuation of application Ser. No. 07/987,506, filed on Dec. 7, 1992, now abandoned.

The present invention relates to the targeted blocking of the genetic information of the viral messenger ribonucleic acid (mRNA) for virus replication (e.g. of HIV) in transfected, haematopoietic cells with particularly suitable expression systems, which express a complementary "antisense RNA".

In particular the invention relates to expression vectors coding for antisense RNA sequences, which, in contrast to the state of the art, produce complete inhibition of HIV-1 replication and clear inhibition of HIV-2 replication in human cells which have been altered using gene technology. The genetic units described here of the expression vectors are particularly suited for the somatic gene therapy of HIV/AIDS diseases, because they protect haematopoietic cells from HIV-induced cytopathic effects. Immune insufficiency in HIV-infected humans can thereby be avoided.

Virus multiplication in an infected cell is regulated by the genes of the virus genome. In this process, regulatory gene products and structural proteins for the construction of infectious virus particles for virus multiplication are formed by these virus genes by means of transcription and translation. The essential intermediate for this process is messenger ribonucleic acid (mRNA), which mediates the information for the formation of the regulatory and structural proteins.

Blocking of the messenger ribonucleic acid in a highly specific manner, which rests entirely on the uniqueness of the molecular structure of the viral mRNA, namely the virus-specific nucleotide-base sequence of this molecule, can be achieved with a ribonucleic acid of complementary base sequence: by sequence-specific nucleotide-base pairing, as has been described in an analogous manner for deoxyribonucleic acid, the previously single-stranded mRNA is complexed in a double-stranded RNA, and the genetic information of the nucleotide-base sequence becomes in part unavailable for protein biosynthesis. The second step of gene expression, i.e. translation, is thereby inhibited. The complementary ribonucleic acid is termed antisense RNA.

The mechanism of the inhibition of gene expression by interactions of the antisense RNA with the target mRNA is complex and to a large extent unclarified. One explanation is the inhibition of RNA splicing and RNA processing in the cell nucleus; detailed investigations on this point are however not known. Evidence of adenosine → inosine exchange in double-stranded RNA has been published, and inhibition of translation suggested as a consequence of this exchange. The inhibition of RNA transport through the perinuclear membrane to the site of protein biosynthesis and the masking of the ribosome/RNA interaction by double-stranded RNA may provide further contributions to the inhibition of gene expression by antisense RNA.

The inhibition of metabolic processes by antisense RNA has been described in naturally occurring biological systems, such as bacteria and some eukaryotic, multi-cellular organisms [K. M. Takayama and M. Inouye, Critical Reviews in Biochemistry and Molecular Biology 25, 155 (1990)], as well as in transgenic organisms produced artificially by gene transfer [J. Mol et al. FEBS Letters 268, 427 (1990)].

There have also been reports on attempts in plants (M. Cuozzo et al., Biotechnology 6, 549 (1988)) and animal cells [T. Rüden and E. Gilboa, J. Virol. 63, 677 (1989), EP 252 940] to produce virus-resistant organisms following the introduction of a gene expressing antisense RNA. There are however no convincing, scientifically proven connections between antisense RNA expression and virus resistance, as the authors themselves state in these publications. In particular, in the case of microinjected plasmids expressing antisense RNA with transient expression the anti-viral activity is weak or leads to anti-viral effects which cannot be conclusively evaluated [K. Rittner et al., Nucleic Acids Research 19, 1421 (1991)]. There has also been a report on the use of retrovirus vectors expressing antisense RNA (R.Y-L. To et al. in: Gene Regulation: Biology of Antisense RNA and DNA ed. R. P. Erickson and J. G. Izant, Raven Press Ltd., New York 1992 for producing virus-resistant cells. These retroviral vectors carry the risk of triggering malignant tumour growth, because they contain oncogene-like gene sequences, and there is multifarious evidence for retrovirus-dependent oncogenesis.

In contrast to the published works on antisense RNA for controlling virus replication, expression constructs are described in the present invention which are distinguished by the particular nature of their promoter constructs in combination with the specially chosen regions of the viral DNA in the antisense orientation, and which thereby provide anti-viral effects of a quality and quantity which are surprising and which surpass by far the scope which has been known hitherto. The combination of expression vector components: 5'-flanking DNA sequence, promoter, insert/antisense DNA and 3'-processing signal sequences led, for the first time with regard to retroviral infections, to quite pronounced and clearly demonstrable virus resistance in transfected cells expressing antisense RNA. By contrast, the state of the art with other vector systems for endogenous antisense RNA expression and retrovirus resistance results in weak anti-viral effects, which only appear transiently [e.g. T. Rüden and E. Gilboa, J. Virol, 63, 677 (1989), EP 252 940, G. Sczakiel et al., Biochem. Biophys. Res. Com. 169, 643 (1990) O. I. Mirosknichenko et al., Gene 84, 83 (1989), (T. Shimada et al., Antiviral Chemistry and Chemotherapy 2, 133 (1991); G. Sczakiel et al. J. Virol. 66, 5576 (1992)], or is affected by the abovementioned risks (retroviral gene transfer) or is impractical because microinjections are necessary.

The invention relates to expression vector constructs for the expression of antisense RNA. which contain hybrid promoter gene sequences and possess a strong constitutive promoter activity or a promoter activity which can be induced in the case of pathogen attack.

These are, for example, those expression vector constructs which contain subgenomic gene sequences of a pathogenic virus in the 3'→5' orientation (antisense orientation of the (+)-DNA strand) under the control of the promoter for the expression of antisense RNA.

Very suitable in the scope of the present invention are those which contain proviral, subgenomic DNA in the antisense orientation from retroviruses such as HIV-1 and HIV-2 or from oncoviruses such as HTLV-I, HTLV-II or from oncogenes such as abl, erb A, erb B, fms, fos, myb, myc, ras, sis and src.

Preferred are expression vector constructs which contain HIV-1 proviral DNA in the antisense orientation of the nucleotides 7514→474 or 5786→474 or 2096→474 or 3825→681 or 5786→4158 or 5746→4648 or 2369→1635 or 3226→3003 or 2099→678 or 3829→2099 or 4647→4157 or 4157→3820.

Expression vector constructs may also be employed which contain subgenic proviral gene sequences or oncogene sequences in the 3'→5' orientation for the expression of shorter antisense-RNA transcripts.

Such expression vector constructs which are to be mentioned here are those which contain proviral gene sequences from HIV-1 of the nucleotides 605→455 or 670→440 or 825→535 or 6070→5800 or 5640→5020 or 5600→5040 or 8690→8300 or 9160→8800.

Preferred are expression vector constructs which contain two, three or more subgenomic gene sequences from one virus or from a plurality of viruses.

The invention also relates to transfected cells which contain the abovementioned expression vector constructs.

The use of the said expression vector constructs for the preparation of medicaments is also within the scope of the invention as are medicaments containing one or more of the expression vector constructs.

Using the herein-described expression vector constructs, an anti-viral effect for HIV replication was demonstrated in relevant human host cells that provides complete protection against HIV-1 replication in human cells for over 60 days and additionally produces significant inhibition of HIV-2 replication.

In the present invention, the construction and composition are described of expression vector constructs which express messenger ribonucleic acid transcripts in transfected cells, which transcripts are complementary to mRNA sequences of unwanted viral genes, using here as examples the genes GAG, POL, VIF, REV, TAT and VPU [W. A. Haseltine et al., Scientific American USA, 1988, 34 to 42], of the human immunodeficiency virus, HIV-1. In addition, the antisense-RNA sequence described is sufficiently homologous towards HIV-2 (e.g. isolate HIV-2 D194, in: Human Retroviruses and AIDS, eds. Myers et al. Los Alamos National Lab., 1992, and EMBL accession No. X52223) in the region of the genes GAG, POL and VIF in order to achieve antiviral effects against HIV-2 isolates as well. The expression vector constructs are distinguished by the particular nature of the arrangement of selected promoter sequences and hybrid promoter sequences (e.g. CMV-IE/ metallothionein I) with subgenomic HIV-1 DNA fragments in the antisense orientation (3'→5') which result in the transcription of several antisense-RNA transcripts by RNA splicing in a constitutive or an inducible manner. Antisense-RNA transcripts formed in this way showed in a surprising manner a drastic or complete inhibition of HIV-1 replication in human cells (HUT 78, U 937 for example). A clear inhibition of HIV-2 replication was also observed. HIV-2 demonstrates sufficient RNA-sequence homology in the expression vector constructs described here to ensure that inhibition of virus replication by antisense RNA is brought about. The invention thus comprises a method for inhibiting the replication of retroviruses, using as examples HIV-1 and HIV-2, which is suitable for protecting haematopoietic cells, and thereby important cells for the human, cell-mediated immune response (e.g. T-cells, monocytes), from cell-damaging and cell-disintegrating virus multiplication by a particular mode of expression of antivirally active antisense RNA.

In order to make cells of the immune system resistant to the cell-damaging effect of retrovirus multiplication, as it is known from HIV-1 and HIV-2 infection, by means of the expression of anti-viral antisense RNA, the experimental procedure was as follows.

Promoters:

Expression vectors were constructed which contain promoters which should express constitutively and strongly in haematopoietic cells, such as, for example, cytomegalovirus IE promoter (CMV-IE). Furthermore, promoters were also constructed, by the fusion of nucleic acid sequences, which should additionally induce amplified expression in the case of virus attack. In particular, a component of these hybrid promoters is the CMV-IE metallothionein promoter fragment and the HIV-1 LTR nucleic acid fragment of the nucleotides 289 to 474 or 289 to 532 (nucleotide numbering: UWGCG GENEMBL DATA BANK File: HIVHXB2CG.VIRAL of the 25th Sep. 1987), which contributes to amplified, optionally transactivatable, supplementary promoter activity.

The antisense nucleic acid fragments

Additionally the vector constructs contain subgenomic, proviral DNA fragments in the antisense orientation, that is, the (+)-strand of the DNA is transcribed in the 3'→5' direction, under the control of the described promoters.

For safety reasons a complete, proviral genomic DNA fragment of a retrovirus is not used. However, longer, subgenomic, proviral DNA fragments rather than short, subgenic, proviral DNA fragments are used in the main, because RNA splicing is more likely to occur in longer RNA transcripts and, in this way, more antisense RNA transcripts are possibly to be expected from the proviral DNA fragments according to the invention, and were indeed found in the examples mentioned. (The type and number of the completely processed antisense mRNA transcripts that are to be expected for the HIV sequences that were used in the antisense orientation is not predictable, because there are no sufficiently accurate consensus sequences for the splicing of mRNA that would permit a conclusive prediction.)

With an increasing number of antisense RNA transcripts, with their inherent properties, such as, for example, export from the nucleus or stability in the cytoplasm, there is also an increasing probability of producing an antisense RNA transcript with potent antiviral activity.

The invention relates additionally to expression vector constructs which contain a fused gene fragment for the transcription of antisense RNA under the control of a strong promoter. The fused gene fragment is composed of subgenomic DNA fragments from two different or several different pathogenic viruses, e.g. from HIV-1 and HIV-2. Using such fused gene fragments, which encode an RNA transcript containing several antisense-RNA sequence regions one after the other which are complementary to mRNA-sequence regions from different viruses, expression vectors can be constructed with a wider anti-viral effect.

The validity of this principle is confirmed by Examples 1, 4, 5, 10 and 12. For example, the expression vector constructs KTX 11, pSXK1 and pSXK2 contain antisense-DNA fragments from HIV-1 LAV/BRU, which themselves contain shorter segments which are also complementary to mRNA from HIV-2 D194 (e.g. nucleotides 620–660 or 837–899 or 4868–5044).

In this way the antisense RNA from KTX11, pSXK1 and pSXK2 is also anti-viral towards HIV-2.

The antisense RNA-encoding sequence of these vectors can be additionally fused with fragments of proviral DNA in the antisense orientation from other viruses (e.g. HIV-2 isolates, other HIV-1 isolates), so that, as a result of the segmentally optimised complementarity of the anti-sense RNA to the sequence of the other viruses, improved or complete inhibition of different viruses can be achieved at the same time with one expression vector construct.

Termination of the antisense-RNA transcripts is achieved with the polyadenylation signal (e.g. from SV 40 or from the bovine growth hormone), in order to generate a highly stable mRNA. Additionally, the vectors contain the complete operon for expression of a suitable selection marker. In the examples presented, an antibiotic resistance TNR 5 neo (neomycin, geneticin, G 418, kanamycin) is used in order to be able to select cells which after transfection contain the genetic construct for antisense-RNA expression.

This selection marker has proved to be of value for human haematopoietic cells. Other selection markers, such as, for example, puromycin or hygromycin or methotrexate in combination with transfection of the gene for dihydrofolate reductase, could also be used.

Particularly suitable as antisense nucleotide sequences are those from the POL/VIF gene region of HIV between nucleotides 2100–5800. In particular, antisense nucleotide sequences of the nucleotides 5786→4158 have been shown to have exceptional anti-viral activity. Other fragments from this gene region can also be used, e.g. 5746→4648 or 4647→4157 or 5880→3880 or 5850→4158 or 5150→3200.

In order to demonstrate the anti-viral effect of the antisense RNA against, for example, HIV-1, human cell lines which can be infected with HIV-1 were transfected with the abovementioned expression vector constructs. The aim was to demonstrate in a series of cell types of human haematopoietic cells that endogenous antisense RNA expression leads to inhibition of virus replication in cells which in particular participate in the cellular immune response. This destruction of cells of the immune system in the terminal phase of the AIDS disease has a causal association with the increased frequency of opportunistic infections, which then often have a fatal outcome. For this reason, the aim of the work with haematopoietic cells, and in this context initially with permanent cell lines such as, for example, HUT 78, MOLT 4, U 937, Jurkat, CEM-CM3 (all American Type Culture Collection ATCC, Bethesda, Md., USA), was, following vector transfection, cloning of the cell lines and genetic characterisation, to determine the "virus resistance" of these transfected cell lines in infection experiments with appropriate HIV-1 and HIV-2 isolates.

The intention was that demonstration of the expression of antivirally active antisense RNA in these cells should indicate the usefulness of the expression constructs in blood-forming cells and in the end also their use for the transformation of cells of the blood-forming bone marrow tissue for therapeutic purposes. The incorporation of genes into peripheral blood lymphocytes and bone marrow cells for therapeutic purposes has already been described elsewhere [K. W. Culver et al., Transplant Proc. 23, 170–177 (1991)] and should in principle be applicable to the herein-mentioned antisense RNA expression constructs.

EXAMPLES

EXAMPLE 1

Expression vector construct KTX 11

(In the following, all nucleotide numbering relates to the human immunodeficiency virus type 1 (HXB2) sequence, UWGCG, GENEMBL DATA BANK, File: HIVHXB2CG.VIRAL of the 25th Sep. 1987, unless otherwise indicated.)

For the endogenous expression of anti-virally active antisense RNA following transfection of HIV-1 infectable cells, the following expression vector was constructed:

The murine metallothionein I promoter [1600 base pairs EcoRI-Bgl II fragment (N. Glanville et al., Nature 292, 267–269 (1982))] was ligated with the Sal I cleavage site (nucleotide 5786) from the 3' region of the proviral HIV-1 DNA sequence following ligation of a Bgl II-Xho I adapter, resulting in modification of the Bgl II, Xho I and Sal I cleavage sites.

The Bgl II cleavage site (nucleotide 474) from the 5' region of the proviral HIV-1 DNA was ligated with a Bam HI cleavage site, to which the sequence of the SV 40 polyadenylation signal is connected (nucleotides 2564 to 4713 with deleted sequences from the UWGCG GenEMBL File SV 40XX). This same polyadenylation sequence from SV 40 is used in the 3'→5' direction for the termination of the TRN5NEO [selection marker neomycin (phosphotransacetylase), nucleotide 1–1286 TRN5NEO BACTERIA, UW GCG GenEMBL]. The neomycin gene expression is initiated by the SV 40 early promoter (nucleotides 5171–371, UWGCG GenEMBL SV 40XX). Otherwise the vector also contains pBR 322 DNA (nucleotides 2067–4363, UWGCG GenEMBL File PBR 322) with bacterial origin and ampicillin resistance gene, in order to be able to use it as a shuttle vector for E. coli and animal cells. A gene map of this vector KTX 11 is presented in FIG. 1.

EXAMPLE 2

Expression vector construct KTX 12

The HIV-1 antisense-RNA expression vector KTX 12 is constructed in the same way as vector KTX 11 (Example 1). However, it contains an inducible hybrid promoter and the HIV-1 template DNA strand extends in the 3'→5' orientation behind this hybrid promoter from nucleotides 7514→474.

Figure 2:
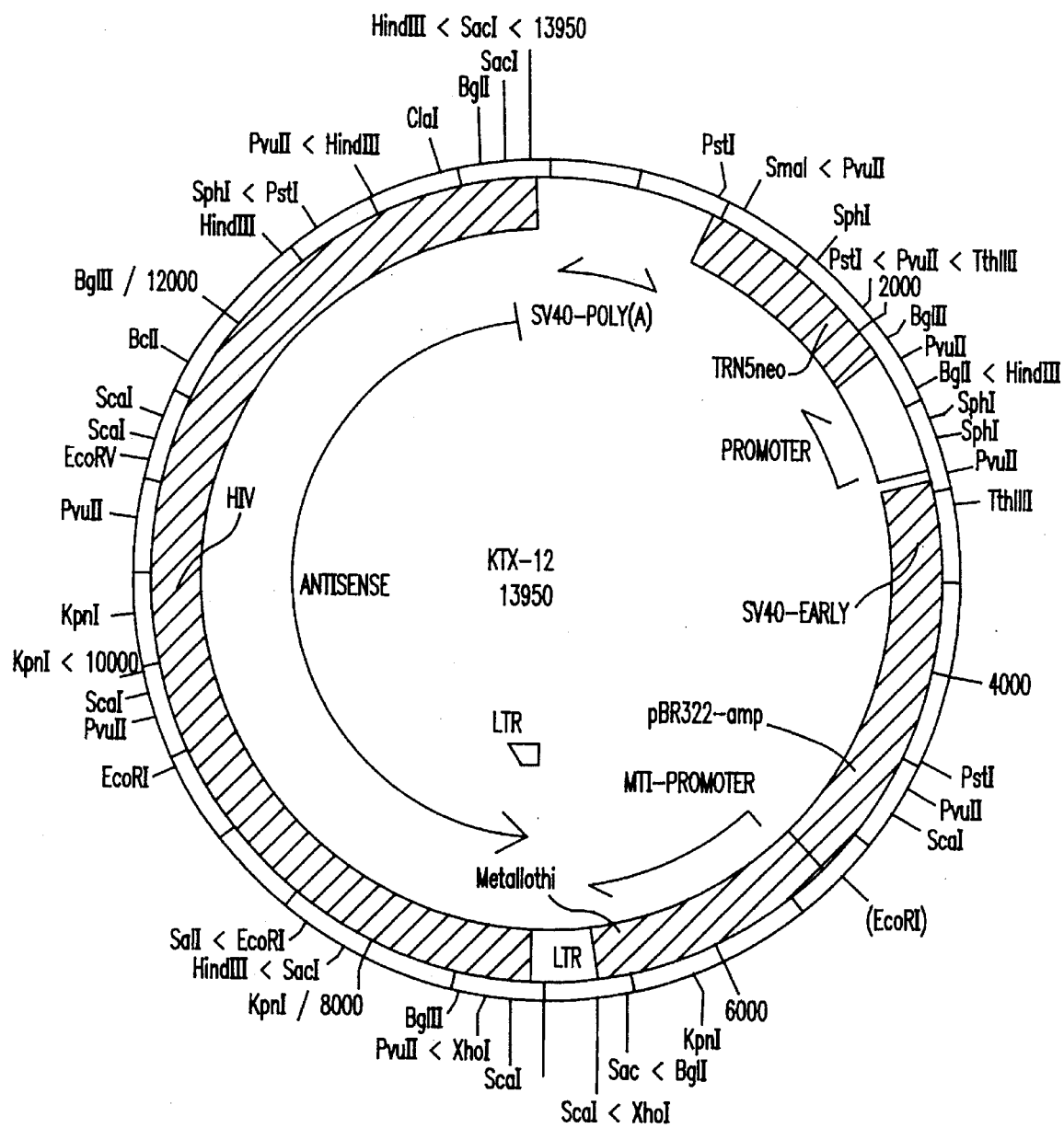

To obtain the hybrid promoter, the HIV-1 LTR promoter fragment nucleotide 289 to 532 was fused onto the metallothionein promoter nucleotide 368 (UW GCG File MUS-METI.RO). A restriction map of this vector KTX 12 is presented in FIG. 2.

EXAMPLE 3

Expression vector construct KTX 15

Figure 3:
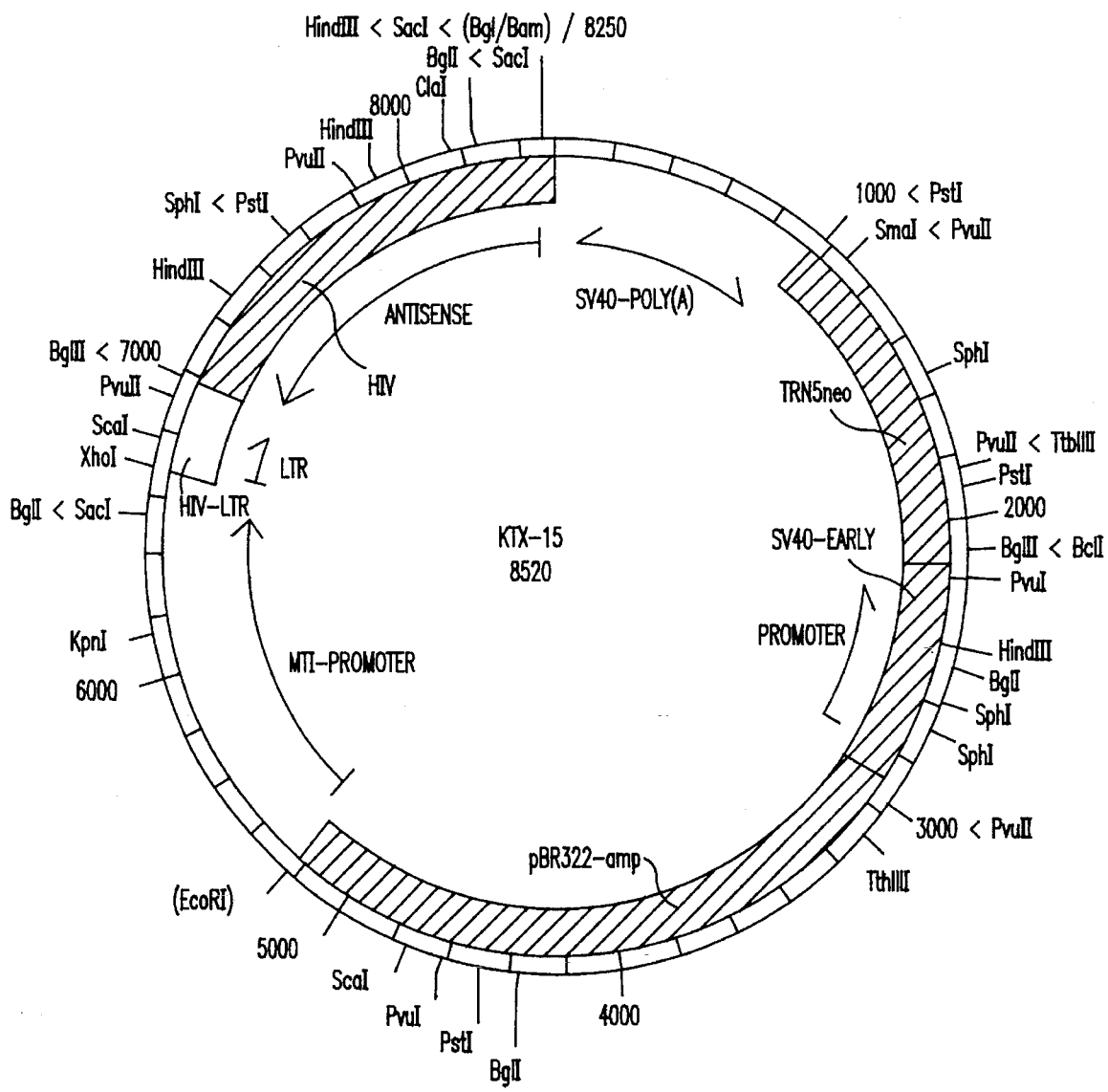

The HIV-1 antisense RNA expression vector KTX 15 is constructed in a similar way to the vector KTX 12 (Example 2). However, the DNA fragment of the HIV-1 template strand (in the 3'→5' orientation) is substantially shortened, extending from nucleotide 2096 to nucleotide 474 and thereby comprising the GAG sequence, the leader sequence, the U5 sequence and a part of the R sequence. A further important property of vector KTX 15 is the deletion of the TAR sequence with the deletion of nucleotides 474–532 in the HIV-LTR hybrid promoter. As a consequence, it should still be possible to activate the hybrid promoter in the case of HIV infection, but the TAR-encoded termination of transcription [S. Y. Kao et al., Nature 330, 489 (1987)] without the presence of the HIV-1 TAT protein should be prevented. This hybrid promoter is thereby distinguished by a particularly high constitutive transcription under the control of an HIV-1 LTR promoter sequence. A restriction map of the vector KTX 15 is presented in FIG. 3.

EXAMPLE 4

Expression vector construct pSXK 1

The HIV-1 antisense-RNA expression vector pSXK 1 has been prepared in order to show expression of antisense RNA under the control of another strong, constitutively expressing promoter, the example here being the cytomegalovirus promoter. The HIV-1 gene fragment nucleotide 681–3825 was inserted in the 3'→5' orientation into the Hind III restriction site at nucleotide 891 (vector pRc/CMV, Catalogue No. V 750–20 from Invitrogen, San Diego, Calif. 92121, USA). The polyadenylation signal comes from the bovine growth hormone (BGH) gene.

Otherwise the vector is constructed as a shuttle vector in the same way as vector KTX 11 (Example 1) with the neomycin selection marker and a pBR322 DNA fragment for replication and selection in E. coli. A restriction map of vector pSXK 1 is presented in FIG. 4.

EXAMPLE 5

Expression vector construct pSXK 2

Figure 5:
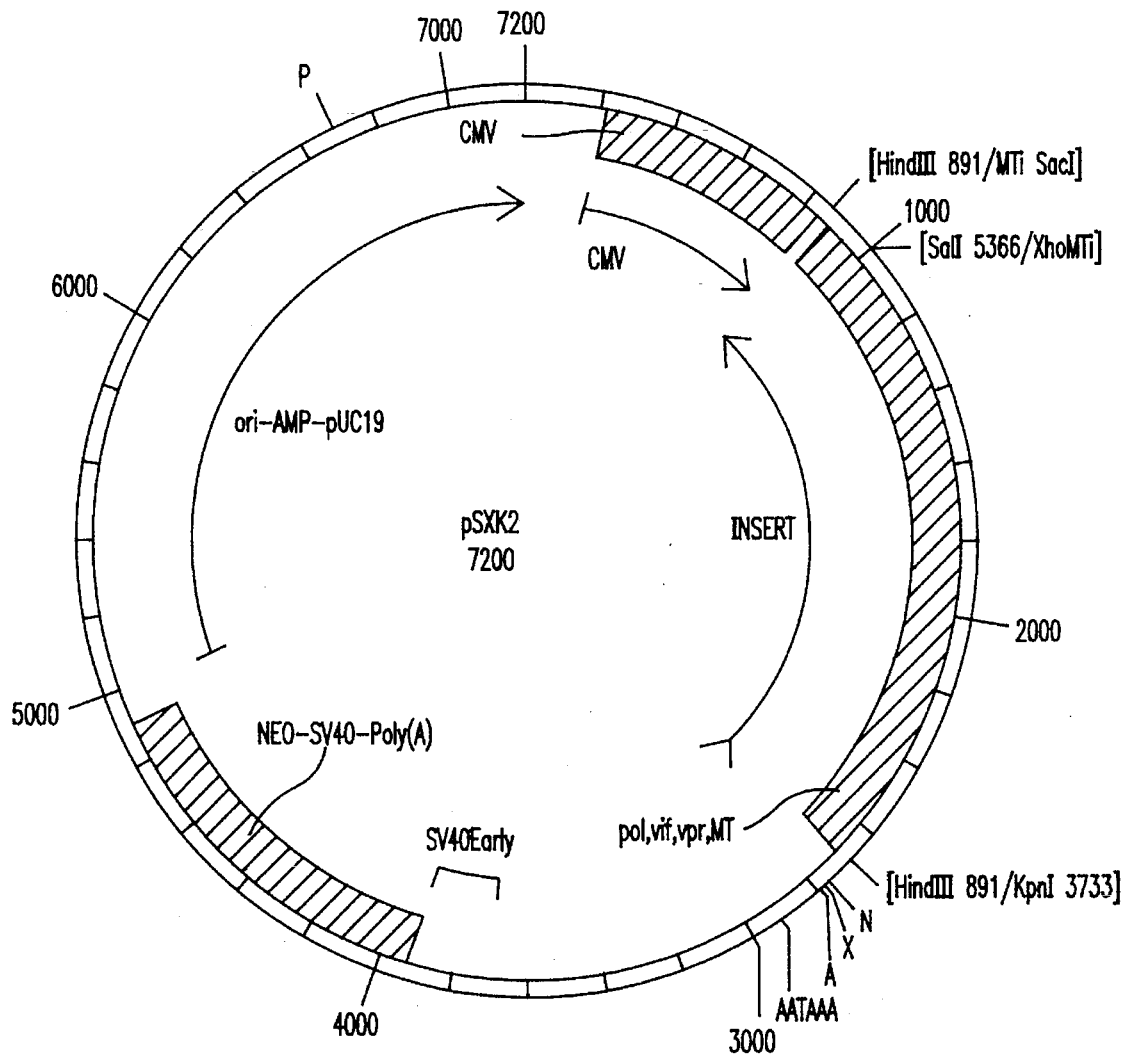

The HIV-1 antisense-RNA expression vector pSXK 2 differs from vector pSXK 1 (Example 4) in that it possesses fused promoter sequences comprising nucleotides 209–865 of the CMV promoter (see Example 4), fused with nucleotides 150–369 of the metallothionein promoter (UWGCG GenEMBL File MUSMETI.RO) and thus also represents a hybrid promoter. In addition, the proviral DNA sequence of the nucleotides 4158–5786 was inserted in the 3'→5' orientation as the template for the antisense-RNA expression under the control of the CMV/metallothionein hybrid promoter. The restriction map of vector pSXK 2 is reproduced in FIG. 5.

EXAMPLE 6

Expression vector constructs pHTT 1, 4, 6, 9, 10, 12 and 15

Figure 4:
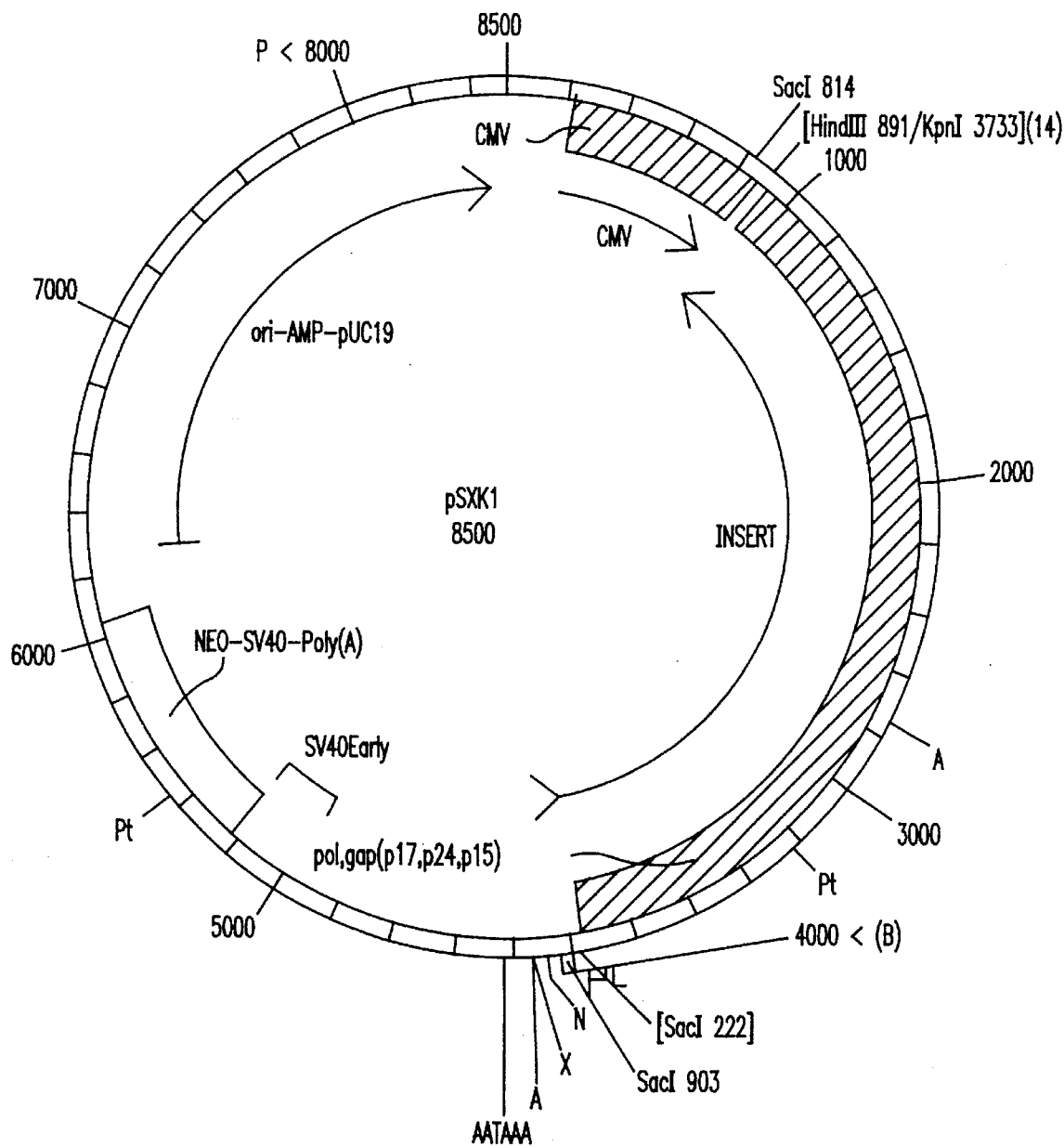

The HIV-1 antisense-RNA expression vectors pHTT 1, 4, 6, 9, 10, 12 and 15 were prepared in a similar manner to vector pSXK 1 (Example 4, FIG. 4). All the HIV-1 gene fragments inserted into the pHTT vectors were cloned in the 3'→5' orientation into vector pRc/CMV (from Invitrogen, San Diego, Calif. 92121, Catalogue No. V 750-20, 1991), under the control of the constitutively expressing cytomegalovirus promoter.

The pHTT vectors are specified below:
  (a) pHTT 1: The HIV-1 gene fragment (nucleotide 4648–5746) was incorporated into the Not I cleavage site (nucleotide 966) of the pRc/CMV vector.
  (b) pHTT 4: The HIV-1 gene fragment (nucleotide 1635–2639) was incorporated into the Xba I cleavage site (nucleotide 985) of the pRc/CMV vector.
  (c) pHTT 6: The HIV-1 gene fragment (nucleotide 3003–3227) was incorporated into the Xba I cleavage site as described under (b).
  (d) pHTT 9: The HIV-1 gene fragment (nucleotide 678–2099) was incorporated into the Xba I cleavage site as described under (b).
  (e) pHTT 10: The HIV-1 gene fragment (nucleotide 2099–3829) was incorporated into the Xba I cleavage site as described under (b).
  (f) pHTT 12: The HIV-1 gene fragment (nucleotide 4157–4647) was incorporated into the Xba I cleavage site as described under (b).
  (g) pHTT 15: The HIV-1 gene fragment (nucleotide 3830–4157) was incorporated into the Xba I cleavage site as described under (b).

Figure 6:
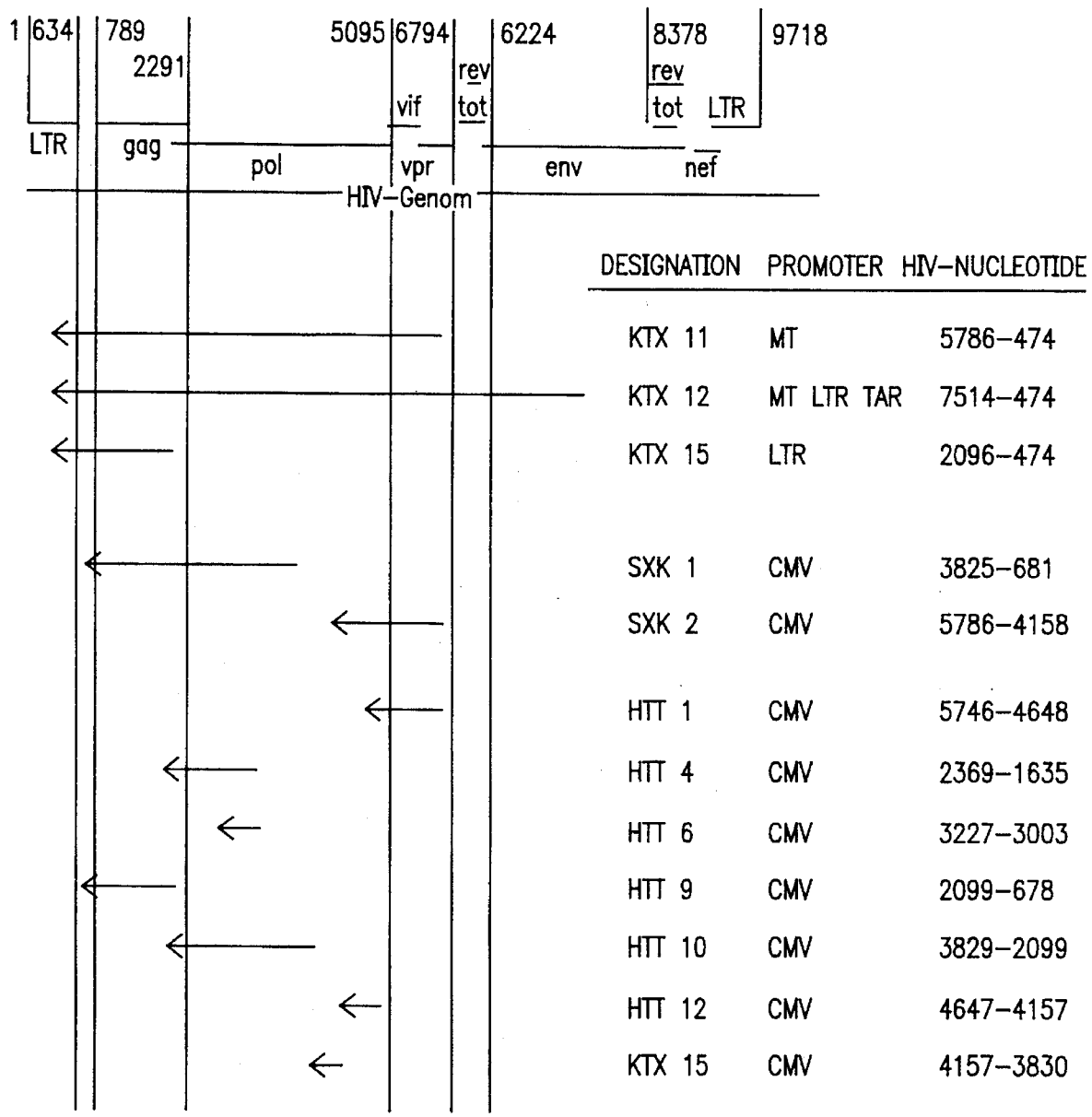

A general diagram of the HIV-1 gene fragments which are contained in the antisense orientation (3'→5') in the vectors of Examples 1 to 6 is reproduced in FIG. 6.

EXAMPLE 7

Transfection and cloning of human lymphocytes with antisense-RNA expression vectors The non-adherently growing, monocyte-like cell line U 937 and the non-adherently growing T-lymphocyte cell line HUT 78 were chosen as examples of transfected human haematopoietic cell lines, which exhibit virus resistance as a consequence of endogenously expressed antisense RNA against HIV-1. Both cell lines were obtained from the American Type Culture Collection (ATCC), 12301 Parklawn Drive, Rockville, Md. 20852-1776, USA.

The cell lines were cultured in the medium recommended by the ATCC. The vector transfection was effected by various methods of which electroporation proved to be the most successful:

1. Calcium phosphate method:
    A variation of the method of Wigler et al., 1977, Cell 11, 223.
    The transfection is carried out with Ca precipitates of the DNA. Varying quantities from 0.05 to 20 µg of DNA were dissolved in 0.25 ml of 250 mM $CaCl_2$ and slowly pipetted into 0.25 ml of 2×HEBS buffer. Transfection was achieved by addition of the whole precipitate mixture to 10 ml of cell culture. 15 hours later the medium was removed by suction. The cells were then shocked with DMSO.
    For a 10 ml culture, 3 ml of a 25% DMSO solution in sterile PBS were added. After 4 min. the liquid was removed by suction and the cells were washed with 5 ml of PBS. Subsequently the cells were taken up in 10 ml of DMEM medium.

2. DEAE-dextran
    On the day before the transfection, the cells were subcultured to a density of $3–4\times10^5$ per ml of culture medium. 2–4 h before the transfection, the cells were centrifuged and taken up in fresh medium. 0.5 to 20 µg of DNA were mixed with 1070 µl of PBS; to this were added 120 µl of a 10 mg/ml DEAE-dextran solution (transfection solution). Before the transfection, 40 ml of the cells were centrifuged, taken up in 10 ml of PBS and centrifuged once again.
    The cell pellet was suspended in 1.2 ml of PBS-DEAE-dextran solution and incubated for 30 min. Subsequently the cells were shocked by addition of 0.8 ml of cold DMSO solution (25% in TBS). After 3 min. 10 ml of TBS were added and the mixture was centrifuged. The cells were washed-in RPMI growth medium and taken up in 40 ml of the same medium.

3. Fusion (Sanari-Goldin method)
    Logarithmically growing cells ($1\times10^7$ cells/ml) were centrifuged and washed once with RPMI medium. 2 ml of a protoplast suspension of E. coli ($2\times10^3$ cells/ml in 10% sucrose and 10 mM $MgCl_2$) were added to the cell pellet. The protoplasts with the transfecting plasmid were prepared by the method of Sanari-Goldin et al. After 8 min. of incubation, centrifugation was carried out and PEG solution (polyethylene glycol 400; 45% solution in RPMI) was then carefully added within 2 min. After 1 min. of incubation, 10 ml of RPMI medium without FCS were added within 7 min. The cells were centrifuged, washed in RPMI medium and taken up in 10 ml.

4. Electroporation
    Electroporation (EP) was carried out with the gene pulser apparatus and capacitance extender from Bio Rad. Logarithmically grown cells were adjusted to a cell density of $1\times10^7$ cells/ml, washed 1×in PBS and resuspended in RPMI medium without FCS with 10 mM dextrose and 0.1 mM dithiothreitol.
    0.4 ml of the cell suspension were placed in an EP cuvette and 10–20 µg of DNA were added. The DNA was dissolved in the proportion of 1 µg of DNA per 1 µl of TE.
    The electroporation conditions were varied as follows:

Capacitance: 260–960 μF; voltage 150–300 V; electrode distance 0.2/0.4 cm; resistance 100–4 ohm.

Before and after the electroporation, the cells were incubated for 10 min. at room temperature, and then subcultured in 10 ml of growth medium +10% FCS.

Selection of transfectants:

The selection of transfectants was in each case carried out on the basis of resistance to G 418.

1. Selection in viscous media.

The transfected cells were first of all pre-incubated in G 418-containing growth medium until no further growth was observable. After that they were sown in viscous medium. Either agar (Gibco) or methylcellulose was used for solidification of the medium. The pre-selected cells were sown onto a tissue culture plate (10 cm), and to this were added 10 ml of selection medium (RPMI +1 mg/ml G 418) and 2 ml of a 2% liquefied agar solution. After the agar had cooled, the plates were incubated in the incubator at 37° C. In a variation of this experiment, the agar was replaced with methylcellulose.

2. Selection with subsequent cloning in a Transwell cell culture chamber (Transwell TM, from Costar)

48 hours after the transfection, the cells were sown on a 96-well microtitre plate at a density of $1 \times 10^5$ cells per 0.2 ml well. G 418 was added at a concentration of 0.7 mg/ml for U 937 and 1.0 mg/ml for HUT 78. As soon as the medium was exhausted, ½ the volume of each well was exchanged for fresh medium; in the case of U 937 only a further 0.5 mg/ml of G 418 was then added.

Incubation was continued until resistant cells were beginning to grow in the individual wells. These mixed clones were expanded to a larger volume and subsequently cloned. For this, a special growth chamber from Costar (Transwell TM, Catalogue No. 3425, 205 Broadway, Cambridge, Mass. 02139, USA) was employed.

The cells were sown at low cell density (50 to 200 cells per 6 ml) in soft agar with G 418 (see Selection in viscous medium) and 6 ml were added to a central chamber (upper compartment). The chamber is separated by a membrane from a very thickly growing fluid feeder culture of U 937 or HUT 78 (200,000 cells/ml) (lower compartment). The fluid medium is partially exchanged after exhaustion, in order to permit further cell growth. As soon as G 418-resistant colonies appeared in the soft agar, they were isolated with a Pasteur pipette and expanded.

In this way, some ten independent, transfected cell lines were cloned, for U 937 and HUT 78, with each of the vectors KTX 11, KTX 12, KTX 15, pSXK 1 and pSXK 2, and further processed for the demonstration of antisense-RNA expression and HIV-1 resistance. In addition, HUT-78 cell lines were generated with the vectors pHTT1, pHTT4, pHTT9 and pHTT10 and examined in HIV-1 infection tests.

EXAMPLE 8

Transformation of bone marrow cells with the expression vector KTX 15

By way of example, the basic procedure for demonstrating transformation of primary bone marrow cells in the mouse model was as follows:

Primary bone marrow cells were isolated from the femurs of six-to ten-week old C57 mice. The cells were taken up in McCoy medium (from Flow) and mixed with interleukin-3 and GM-CSF (granulocyte-monocyte colony stimulating factor; from Genzyme), in each case at a concentration of 2.5 μg/ml, and agar (Bacto agar, from Difco; final concentration 0.3%), and plated out at a concentration of $1 \times 10^5$ cells per ml in the presence or absence of the toxic antibiotic G418 (neomycin) in Petri dishes. A transfection was carried out directly after the removal of the bone marrow cells before plating out in agar. Subsequently the cells were cultured for several days at 37° C. in the incubator and at 7.5% $CO_2$. After various time intervals, the number of transformed colonies (at least 50 cells) or clusters (10 to 50 cells) were in each case counted under the microscope. Under the given experimental conditions, most of the colonies were mixed granulocyte/monocyte or granulocyte colonies; erythroid bursts were occasionally observed, as were megakaryocytes on one occasion. The identification of the cell types in the colonies was carried out by May-Grünewald staining.

The transfection conditions were optimised. Successful transfections of primary bone marrow cells were obtained under the following conditions: 800 μl of bone marrow cell suspension ($5 \times 10^6$ cells in electroporation medium as described in Example 7), 5 μg of KTX15, electroporation at 300 V, 100 Ω, 250 μFD, 6 ms.

After the electroporation (gene pulser apparatus and capacitance extender from Bio Rad), the cells were selected in the abovementioned culture medium in the presence of 500 μg/ml G-418 (neomycin). Resistance to G-418 indicated successful transfection of propagatable primary bone marrow cells. EXAMPLE 9

Figure 7:
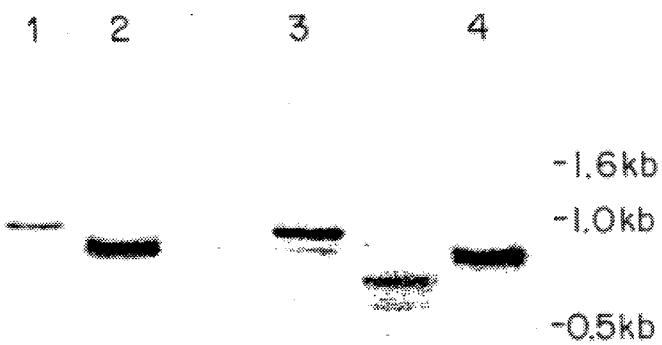
Figure 8:
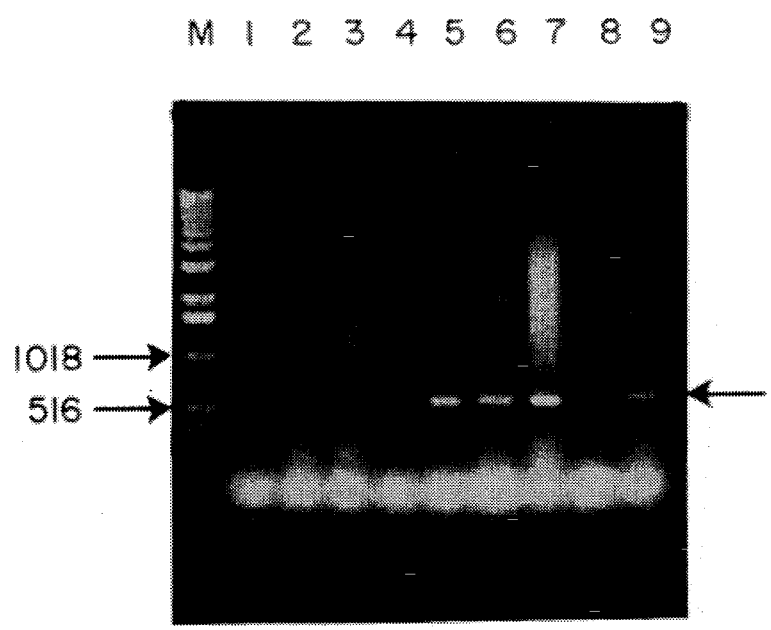
Figure 9A:
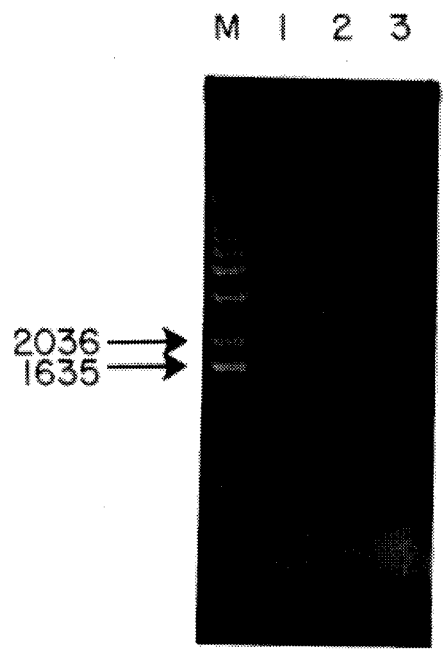
Figure 9B:
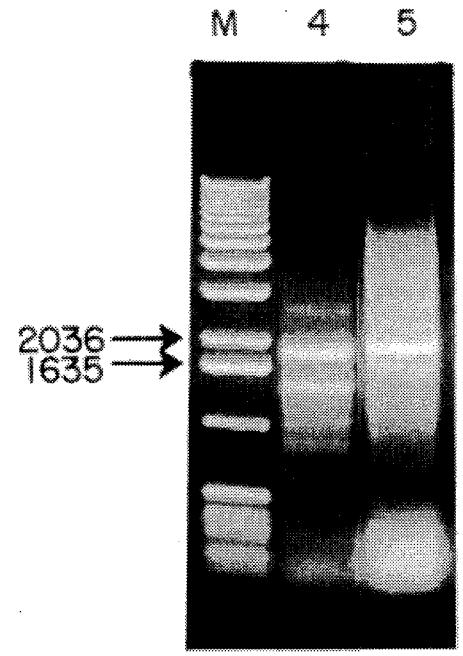

Demonstration of the integration of intact expression vector constructs and demonstration of antisense-RNA expression Following disruption of the transfected U 937 and HUT 78 cell lines, the DNA and RNA from these cell lines was isolated by standard methods using caesium chloride density-gradient centrifugation [L. G. Davis et al., Basic Methods in Molecular Biology, Elsevier, N.Y. (1986)]. Demonstration of the integration of intact vector constructs for antisense-RNA expression was carried out by means of the polymerase chain reaction [PCR Technology Principles and Application for DNA Amplification, Ed. Henry A. Erlich, M. Stockton Press, New York (1989)] using oligonucleotide primers which amplified overlapping DNA fragments of promoter sequence, insert sequence and termination sequence. Subsequently the amplified DNA was identified by means of Southern blot analysis (Davis et al., see above) using DNA insert gene probes. Examples of analytical results are given in FIGS. 7, 8 and 9. For example, the flanking primers 5'-CAA ACC CTT TGC GCC CG-3' or 5'-ACT CGT CCA ACG ACT AT-3' from the promoter sequence and 5'-TTT TTT CAC TGC ATT CTA CTT-3' from the polyadenylation sequence were used for the vectors KTX 11, KTX 12 and KTX 15. In the case of the expression vectors with the pRc-CMV vector, the flanking primers 5'-CTT TCC AAA ATG TCG TAA CAA CTCC-3' and 5'-ATT TAG GTG ACA CTA TAG AAT-3' were, for example, used for the promoter sequence and for the termination sequence, respectively. In the insert (HIV sequence) primer sequences were chosen which yielded PCR products of about 500 base pairs to 2,100 base pairs depending on the choice of primer pairs.

Figure 10:
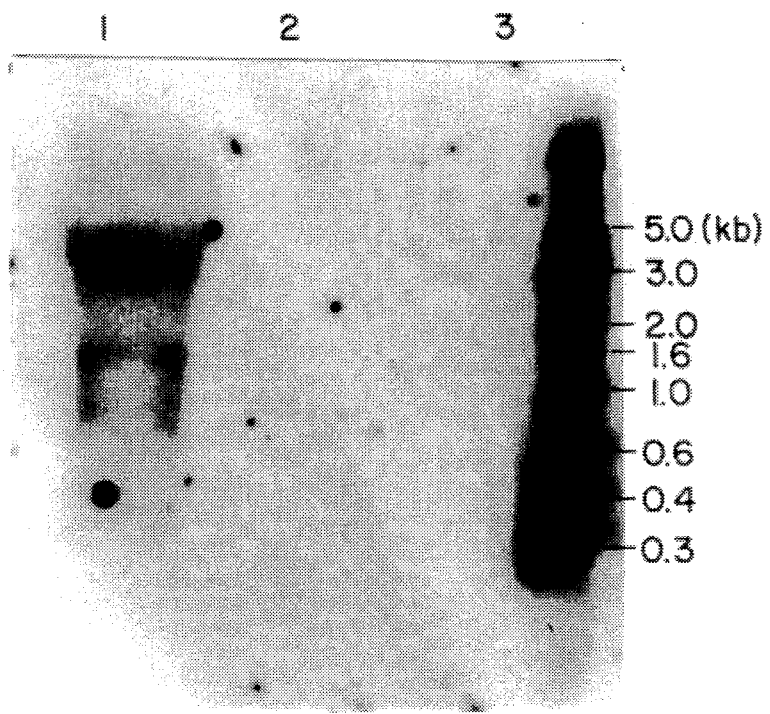

Demonstration of antisense-RNA expression was carried out by Northern blot analyses (Davis et al., see above) of RNA from the cloned, transfected cell lines. An example of an analytical result for the demonstration of HIV-1 antisense RNA in a transfected U 937 cell line is given in FIG. 10.

EXAMPLE 10

Demonstration of the virus resistance of transfected, cloned haematopoietic cell lines Cloned, antisense RNA-expressing cell lines, which were obtained and characterised according to Examples 7 and 9, were examined for the expression of virus resistance in comparative infection studies with HIV-1 (L. Ratner et al., Nature 315, 277 (1985)] or HIV-2 D 194 (H. Kühnel et al., Nucleic Acids Research (990) 18, 6142) together with the starting cell lines HUT 78 and U 937 as controls.

1. Infection of HUT 78 and U 938 cells with HIV-1 (controls)

Procedure

In each case 10 ml of cell suspension were treated for 60 min. with different dilutions of HUT 78/HIV-1 culture supernatant (about $10^4$ SFU/ml in PBL cultures, RT activity of the frozen stock solution 650, 000 cpm/ml). The cells were subsequently centrifuged off and washed three times in order to remove unbound virus particles and virus proteins. Finally the cells were in each case resuspended in 10 ml of culture medium and cultured in the incubator.

Every 3 to 4 days, 200 µl of the cell-free culture supernatant were tested for the presence of HIV antigens. An antigen-capture assay from Organon Technika was used.

To maintain the cells, 5 ml of cell suspension were in each case removed and replaced with 5 ml of culture medium.

2. Infection of antisense RNA-expressing HUT 78 cells and U 937 cells with HIV-1

Procedure

In each case 10 ml of cell suspension (about $4 \times 10^5$ cells/ml) were treated for 60 min. with diluted culture supernatant from HUT 78/HIV-1 (about $10^4$ SFU/ml in PBL cultures, RT activity of the frozen stock solution 650,000 cpm/ml); the final dilution of the stock virus solution was 1:1,000 for the HUT 78 cells and 1:50 for the U 937 cells. The cells were subsequently centrifuged off and carefully washed four times in order to remove unbound virus particles and virus proteins. Finally the cells were resuspended in each case in 10 ml of culture medium (RPMI 1640 +16% FCS) and cultured for 60 days in the incubator.

Every 3 to 4 days, 160 µl of the cell-free culture supernatant were tested for the presence of HIV antigens. An antigen capture assay from Organon Technika was used with the accompanying microtitre plate photometer.

To maintain the cells, 5 ml of cell suspension were in each case removed every 3 to 4 days and replaced with 5 ml of fresh culture medium.

As representative results for other HIV antisense RNA-expressing cell lines, two series of experiments with three HUT 78 transfectants (HUT K14-KTX11, SSHUTK16/2-SXK1,SSHUTK1/1-SXK2) (see FIG. 11) and with three U 937 transfectants (ssUK 20/4-KTX11 a, ssUK 3/1-SXK2 and ssUK 20/15-KTB11b) (FIG. 12) may be mentioned which show no indications of HIV multiplication after infection during an incubation period of up to 60 days in these antisense RNA-expressing cell lines harbouring the expression vectors pSXK1 and pSXK2, whether reverse transcriptase activity (RT activity) or an HIV antigen is measured in these cell cultures. By contrast, HIV multiplication is clearly measurable in the Control cell line. Additionally, a delayed increase in virus replication can be observed in transfectants with the more weakly expressing expression vector KTX11. The result is presented in FIGS. 11 and 12.

Figure 13:
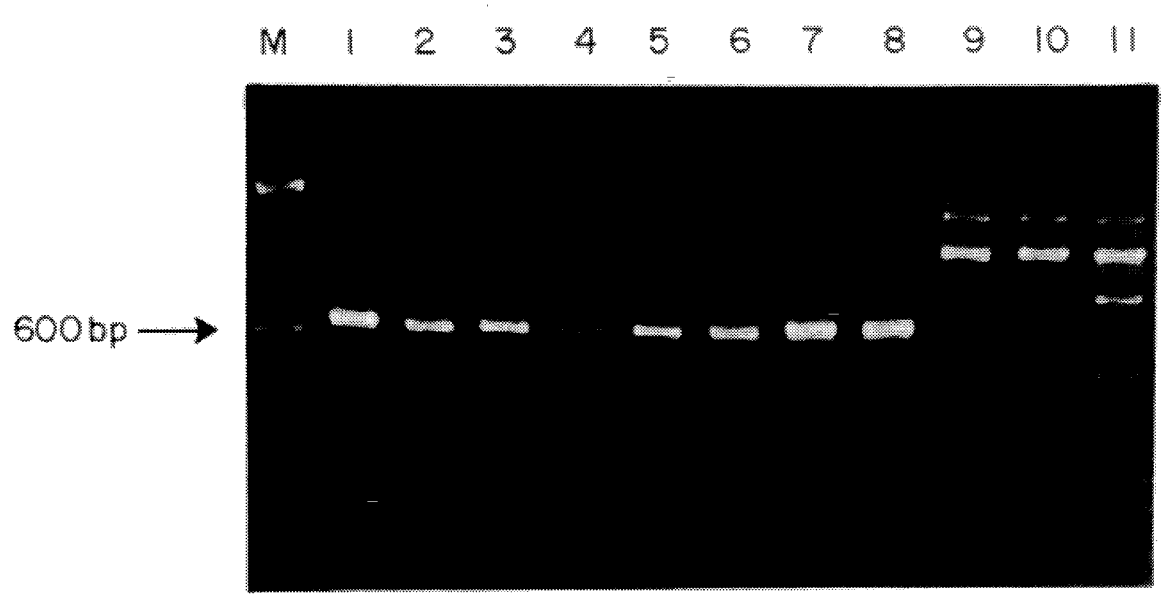

In order to check for HIV-1 infection having occurred in the cell lines SSU K3/1-SXK2, SSHUT K16/2-SXK1 and SSHUT K1/1-SXK2, in which no HIV-1 antigen or RT activity could be detected after 60 days of incubation, positive identification was demonstrated, for example, by PCR detection of HIV-1 TAT gene sequences and envelope gene sequences in the cells of SSHUT K16/2-SXK1 and SSHUT K1/1-SXK2 which had been incubated for 60 days (FIG. 13). For this purpose the PCR primers 5'-ATG GAG CCA GTA GAT CCT-3' and 5'-TCT ACC ATG TCAT-3' were used to generate a 690 base pair-long PCR fragment. The expression vectors pSXK1 and pSXK2 do not contain these sequences and cannot therefore yield any false-positive PCR product.

EXAMPLE 11

Control experiments

Transfection of the vectors from Examples 1 to 6 without the inserts of proviral DNA from HIV-1 in the antisense orientation did not, in the cell lines U 937 and HUT 78, lead to cell lines in which virus replication was inhibited. Control experiments with the vectors from Examples 1 to 6, in which, however, the proviral HIV-1 DNA fragment is inserted in the sense orientation, were not carried out, because the corresponding sense transcripts can bind regulatory proteins of HIV replication, such as, for example, TAT and REV, and thereby inhibit virus replication competitively [G. J. Graham et al., PNAS 87, 5817 (1990)] and thus appear unsuitable as control experiments.

EXAMPLE 12

Infection of antisense RNA-expressing HUT 78 and U937 cell lines with HIV-2

Infection experiments were carried out with the isolate HIV-2 D194 (H. Kühnel et al., Nucleic Acids Res. 18 (1990) 6142). The virus strain suspension with an RT activity of $2.14 \times 10^5$ cpm/ml and an antigen concentration (1:1,000 dilution) of 0.249 $OD_{450nm}$ (160 µl sample) was stored at −80° C. 50 µl of this virus strain suspension were employed for the infection of $2 \times 10^6$ HUT 78 cells in 4 ml of culture medium, which was incubated for 3 hours. In the case of U937 cells, $2 \times 10^6$ cells were incubated for the infection with 100 µl of virus strain suspension in 4 ml of culture medium for 24 hours. Subsequently, unbound virus particles were removed from the cell culture by washing.

At intervals of 3 to 4 days the cell cultures were maintained and cell culture supernatant was removed for quantitative HIV antigen determination with the HIV antigen-capture assay from Organon Technika in association with the accompanying microtitre plate photometer. The course of HIV-2 D194 replication in the HUT 78 control cell lines and U937 control cell lines, which do not contain antisense-RNA expression vectors, is compared in FIGS. 14 and 15 with that in the transfected cell lines, which demonstrate delayed HIV-2 multiplication as a result of antisense RNA-expression.

Results

With the expression vectors KTX 11, KTX 12, KTX 15, pSXK 1, pSXK 2, pHTT 1, pHTT 4, pHTT 6, pHTT 9, pHTT 10, pHTT 12 and pHTT 15 (Examples 1 to 6), and following gene transfection and cloning of transfected cell lines (Example 7), antisense RNA against HIV-1 was formed endogenously in human blood cell lines (Example 9) and its antiviral effect was demonstrated (Examples 10, 12).

Figure 11:
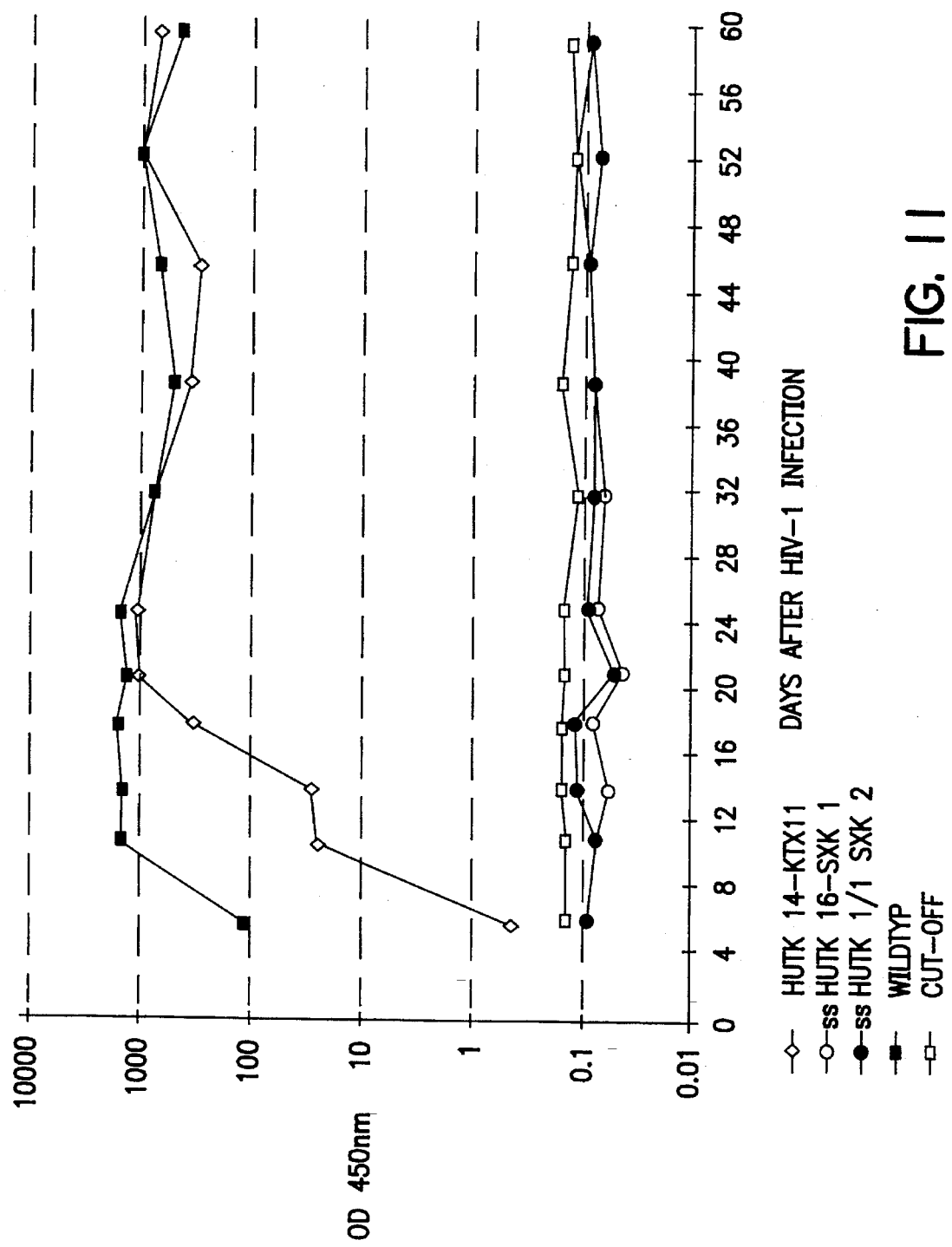
Figure 14:
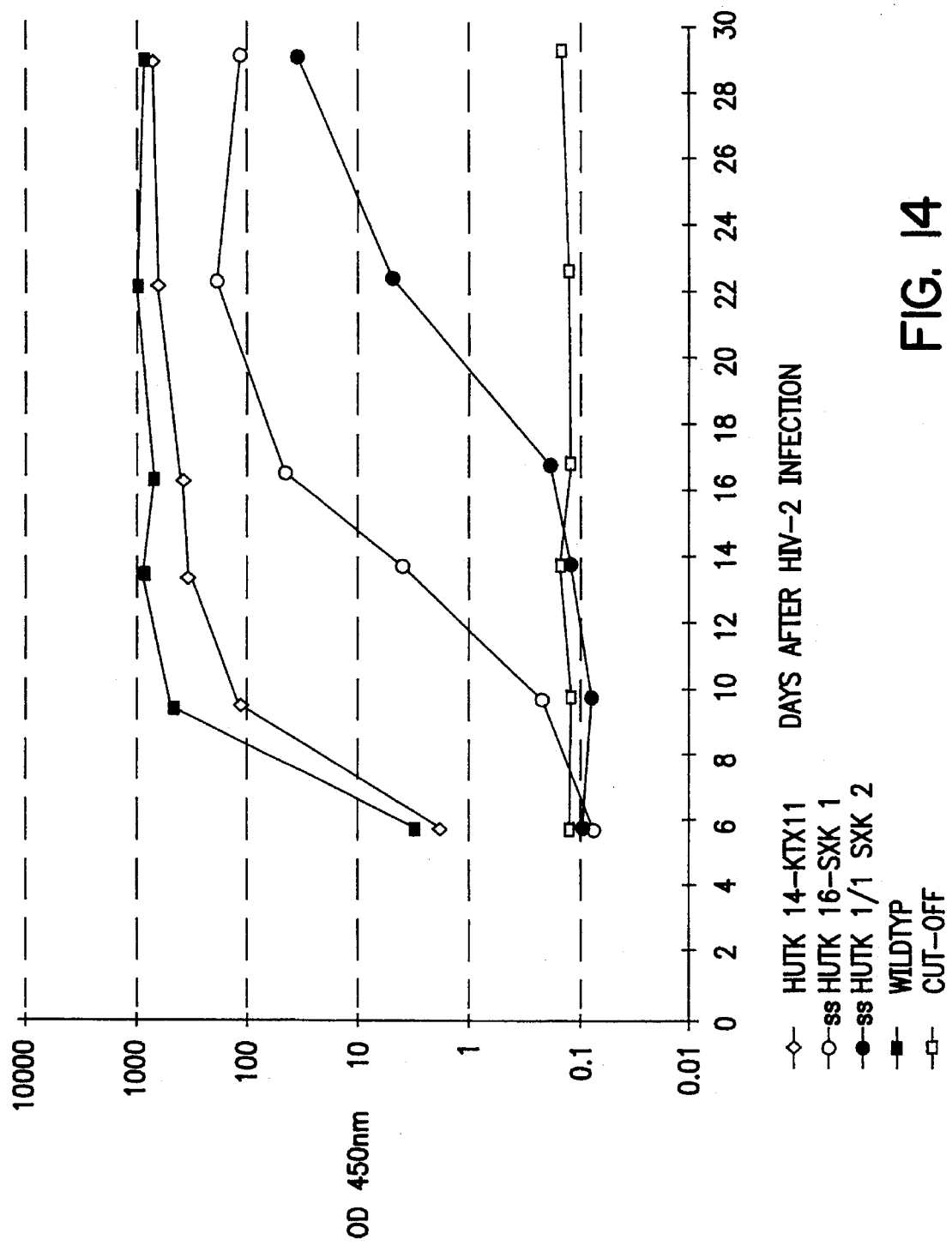
Figure 15:
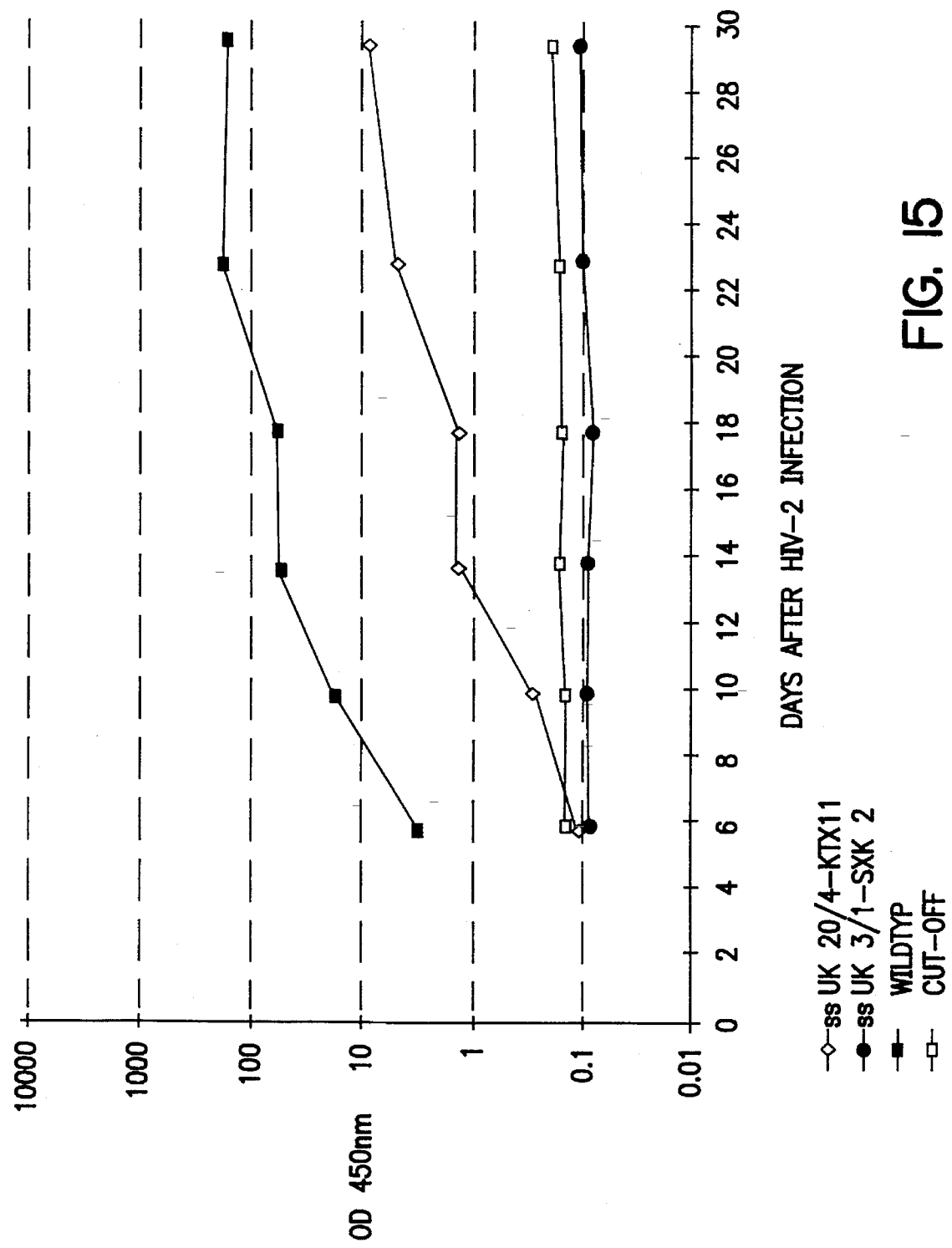

It is surprising that a clearly expressed inhibition of the replication of the retrovirus HIV-1 was demonstrated in the transfected cell lines. The virus resistance of the antisense RNA-expressing cells could also be shown in a similar manner with an HIV-1 virus which was specially adapted to the transfected cell lines (FIG. 11, 12). A marked antiviral property of the antisense RNA was also observed against HIV-2 (FIG. 14, 15).

These results show, by way of example, that suitable promoters for the expression of antisense RNA molecules, and naturally also the nature of the antisense-RNA sequences, lead to the development of resistance against retrovirus attack in genetically altered cells. It was shown in Example 9 that, because of previously unknown RNA splicing of HIV-1 RNA transcripts of the (+)-strand of the proviral HIV-1 DNA in the 3'→5' orientation, several mRNA molecules arise which lead to the anti-viral effect.

By means of the experiments which were described in Examples 1 to 12, it was shown that, using suitable expression vector constructs with antisense RNA-encoding DNA fragments from a retrovirus, antiretroviral properties can be produced in cells and these properties protect against retrovirus attack.

Figure 12:
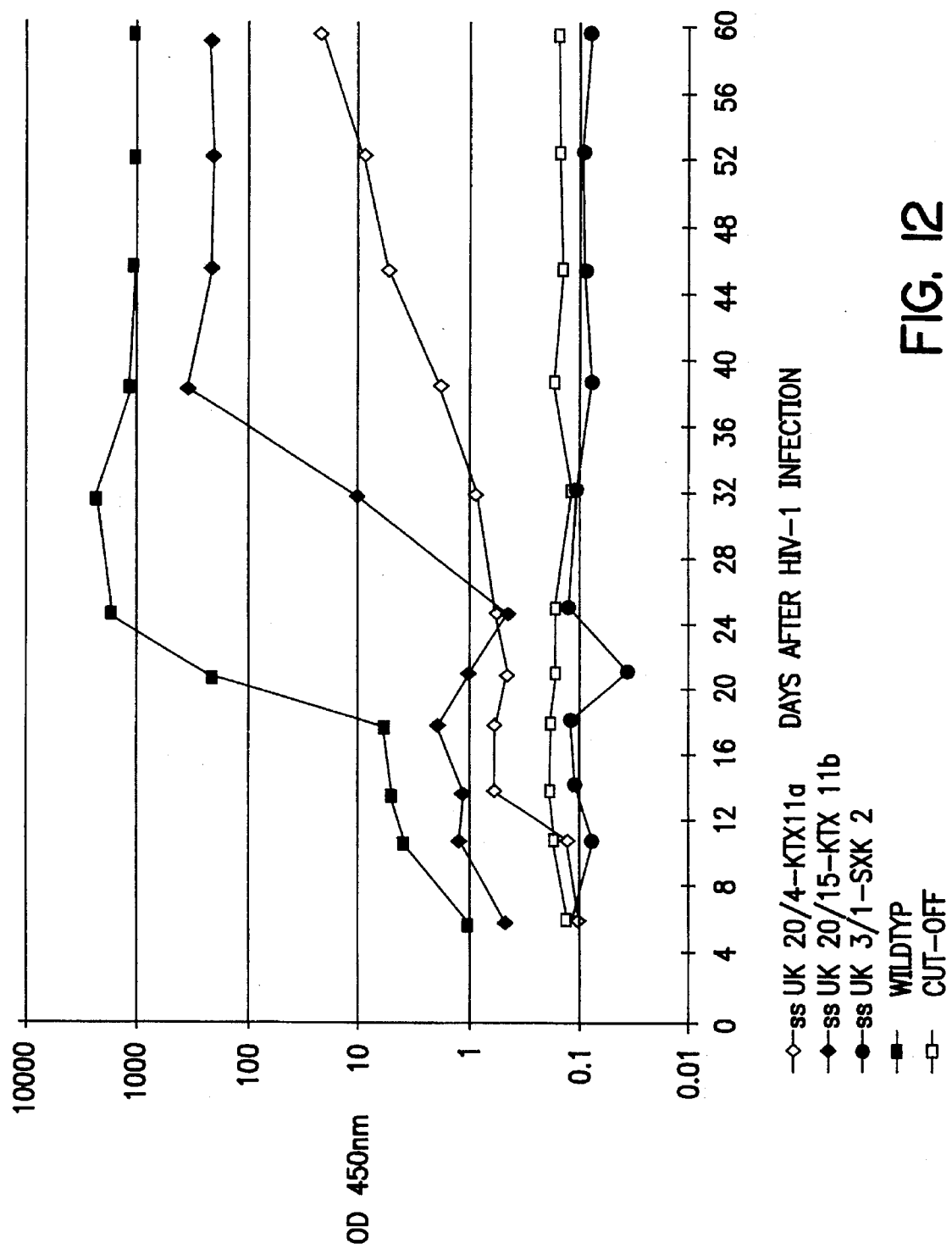

From FIGS. 11 to 13, it is evident that the cell lines SSHUT K16/2-SXK1 and SSHUT K1/1-SXK2 are, 60 days after HIV infection, positive for the detection of proviral HIV DNA by means of PCR analysis, but negative as regards the detection of HIV antigen. This result leads to the conclusion that, following HIV-1 infection of the cells, proviral DNA is indeed still formed in the transfected HUT 78 cell lines in the first step of the HIV replication cycle, but that the transcription/translation of proviral DNA is prevented by the antisense RNA and no HIV protein for virus replication is formed in detectable amounts.

In the DNA of the cell line SSU K3/1-SXK2, neither the formation of HIV proteins or proviral HIV DNA could be detected in any of the test samples, using the antigen test and PCR analysis, respectively, at 60 days after infection with HIV-1. This result may be interpreted as indicating that the antisense RNA formed in the cell line SSU K3/1-SXK2 not only suppresses the second step in the HIV replication cycle (the transcription and translation of proviral DNA), but also even inhibits the first step in the replication cycle:

The formation of proviral DNA from the genomic (+)-strand RNA by the process of reverse transcription can evidently be prevented by antisense RNA. This effect of antisense RNA has been speculatively assumed, but could not be demonstrated previously (R. Y. L. To and P. E. Neiman in Gene Regulation: Biology of Antisense RNA and DNA eds. R. P. Erickson and J. G. Izant, Raven Press Ltd., N.Y. 1992), because correspondingly powerful expression vector constructs have not hitherto been discovered.

Legends
FIG. 1

Expression vector KTX 11 for the expression of HIV-1 antisense RNA. The metallothionein promoter (MTI promoter) drives the transcription of antisense RNA from a proviral HIV-1 DNA fragment of the nucleotides 5786→474 (numbering: UWGCG GENEMBL DATA BANK File HIV HXB2CG. VIRAL. The antisense-RNA transcripts are terminated by the SV 40 polyadenylation sequence. The neomycin resistance gene TRN5neo is transcribed by the SV 40 early promoter. The shuttle vector also contains the pBR322 origin and the ampicillin gene (pBR 322-amp). Further details are described in Example 1.

FIG. 2

Expression vector KTX 12 for the expression of HIV-1 antisense RNA under the control of an HIV-1LTR metallothionein hybrid promoter. Details of the construction of the vector are described in Example 2.

FIG. 3

Expression vector KTX 15 for the expression of HIV-1 antisense RNA under the control of an HIV-1LTR metallothionein hybrid promoter, in which the HIV-1 TAR sequence is deleted in order to achieve maximum expression without the presence of the transactivator protein TAT. Details of the construction of the vector are described in Example 3.

FIG. 4

Expression vector pSXK 1 for the expression of HIV-1 antisense RNA under the control of the cytomegalovirus promoter (CMV). Details of the construction of the vector are described in Example 4.

FIG. 5

Expression vector pSXK 2 for the expression of HIV-1 antisense RNA under the control of the cytomegalovirus promoter (CMV). The proviral HIV-1DNA fragment from the central genomic region of HIV does not, in this example, contain sequences of the 5' region as in Examples 1 to 4, but instead a sequence from the POL/VIF region. Details of the construction of the vector are given in Example 5.

FIG. 6

Basic diagram for the preparation of HIV-1 gene fragments, which are contained in the 3'→5' antisense orientation (arrow direction) in the antisense-RNA expression vectors with the designation given in column 1. The promoter of the respective expression vector is indicated in column 2, and the nucleotide numbering of the HIV sequence according to UWGCG GENEMBL DATA BANK File: HIVHXB2CG.VIRAL is indicated in column 3.

FIG. 7

Southern blot analysis, following PCR amplification, of chromosomal DNA from a cloned U 937 transfectant which contains the expression vector pSXK1 integrated into chromosomal DNA. The intact nature of the promoter/insert sequence is indicated by the fragment size of the PCR products and the hybridisation with an HIV gene probe, which does not contain the primer sequence of the PCR products.

1 Control sample vector, 5'-junction, 887 base pair fragment

2 Control sample vector, 3'-junction, 775 base pair fragment

3 Chromosomal DNA, 5'-junction, 887 base pair fragment

4 Chromosomal DNA, 3'-junction, 775 base pair fragment

Further details are given in Example 9.

FIG. 8

Detection of the HIV-1 gene fragment in chromosomal DNA from cloned BUT 78 transfectants by means of PCR amplification. The PCR reaction was separated on an agarose-TAE gel and photographed under UV light following ethidium bromide staining. The PCR product contains 561 bp and corresponds to the HIV-1 gene fragment (nucleotides 699–1305), which is also a component of the pSXK1 vector. The 561 bp-long PCR product is indicated by an arrow.

M=DNA length standard, 516 bp and 1018 bp are indicated

1=negative control, no DNA was added to the PCR reaction

2=chromosomal DNA from U937 cells (wild type)

3=chromosomal DNA from HUT 78 cells (wild type)

4=negative control, no DNA was added to the PCR reaction

5=positive control

6=chromosomal DNA from HUT 78 transformants (SSHUT 6/1 107-9/1)

7=chromosomal DNA from HUT 78 transformants (SSHUT 6/1 107-9/1)

8=chromosomal DNA from HUT 78 transformants (SSHUT 6/1 107-9/1)

9=chromosomal DNA from HUT 78 transformants (SSHUT 6/1 107-9/1)

FIG. 9

Detection of the HIV-1 gene fragment (nucleotides 4158–5792) in chromosomal DNA from U937 monocyte cells and HUT 78 T-lymphocyte cells by means of PCR amplification. The cells had previously been transfected with the pSXK2 vector. The PCR reaction was separated on agarose-TAE gel and photographed under UV light following ethidium bromide staining. The PCR product contains the whole HIV-1 gene fragment in pSXK2 (nucleotides 4158–5792) and is 1811 bp long. The 1811 bp-long PCR product is indicated by an arrow.

M=DNA length standard, 1635 bp and 2036 bp length standards are indicated

1=negative control, no DNA was added to the PCR reaction

2=chromosomal DNA from U937 cells (wild type)

3=chromosomal DNA from HUT 78 cells (wild type)

4=chromosomal DNA from HUT 78 transformants (SSHUT 2/1 107-12/1)

5=chromosomal DNA from U937 transformants (SSUK 3/1 107-12/1)

FIG. 10

Northern blot analysis for demonstrating several antisense RNA transcripts in a transfected, cloned U 937 cell line, which contains the expression vector KTX 11 in the cell line SSUK 20/15-KTX11 b. Using a gene probe which corresponds to the HIV-1 insert DNA of the vector KTX 11, at least three antisense-RNA transcripts of 800 bp, 1,200 bp and 3,200 bp in length can be detected in the RNA of the virus-resistant cell line (track 1). Track 2 contains RNA from the non-transfected cell line U 937 (negative control). Track 3 contains RNA molecular weight standards.

FIG. 11

Course of HIV-1 antigen formation over 60 days following the infection (on day zero) of HUT 78 cell lines with HIV-1LAV/BRU isolate. The optical density at 450 nm (OD 450 nm) resulting from the HIV ELISA test carried out on the cell culture supernatant is given on the ordinate. At an optical density >2.0, the culture supernatant was diluted and the indicated OD value was calculated from the dilution. The cut-off value represents the detection limit for the HIV antigen-determination.

In the antisense RNA-expressing cell lines SSHUT K16/2-SXK1 and SSHUT K1/1-SXK2, HIV replication is completely inhibited over a time period of 60 days.

In the cell line HUT K14-KTX11, onset of HIV replication is delayed as compared with the non-transfected wild-type cell line HUT 78.

FIG. 12

Course of HIV-1 antigen formation over 60 days following infection (on day zero) of U937 cell lines with HIV-1 LAV/BRU isolate. The optical density at 450 nm (OD 450 nm) resulting from the HIV ELISA test on the cell culture supernatant is given on the ordinate. At an optical density >2.0, the culture supernatant was diluted and the indicated OD value was calculated from the dilution. The cut-off value represents the detection limit for the HIV antigen determination.

In the antisense RNA-expressing cell line SSUK3/1-SXK2, HIV replication is completely inhibited over a time period of 60 days. The other transfected cell lines exhibit delayed HIV replication in comparison with the wild-type cell line ( U937 ).

FIG. 13

PCR analysis for detecting HIV-1 DNA in cell lines which contain antisense-RNA expression vectors and which were analysed 60 days after HIV infection. The ethidium bromide-stained agarose electrophoresis gel shows the PCR products from the chromosomal DNA of the cell lines indicated below.

A 702 base pair-long PCR fragment from the TAT-ENV gene region was amplified in HIV-1 infected cell lines using the primer pair 5'-ATG GAG CCA GTA GAT CCT-3' and 5'-TCT GT TCT ACC ATG TCAT. For comparison with the PCR result, the result of the HIV antigen test for the corresponding cell culture sample is given in brackets.

Track M: Molecular weight standard, 600 bp is indicated

Track 1: HUT K14-KTX11 702 bp positive (antigen test positive ).

Track 2: SSHUT K16/2-SXK1 702 bp positive (antigen test negative).

Track 3: PCR product from a parallel infection experiment to track 2

Track 4: PCR product from a parallel infection experiment to track 2

Track 5: SSHUT K1/1-SXK2 702 bp positive (antigen test negative)

Track 6: PCR product from a parallel infection experiment to track 5

Track 7: Parallel infection experiment to track 5

Track 8: HUT 78, positive control

Tracks 9–11: SSUK3/1-SXK2 cultures: no 702 bp PCR product detectable (antigen test negative)

FIG. 14

Course of HIV antigen formation over 30 days following infection (on day zero) of HUT 78 cell lines with HIV-2 D194 isolate. The optical density at 450 nm (OD 450 nm) resulting from the HIV ELISA test from the cell culture supernatant is given on the ordinate. At an optical density >2.0, the culture supernatant was diluted and the indicated OD value was calculated from the dilution. The cut-off value represents the detection limit of the HIV antigen determination.

In the antisense RNA-expressing cell line SSHUT K1/1-SXK2, HIV replication is completely inhibited over a time period of 14 days. The other transfected cell lines show delayed HIV replication in comparison with the wild-type cell line (HUT 78).

FIG. 15

Course of HIV antigen formation over 30 days following infection (on day zero) of U937 cell lines with HIV-2 D194 isolate.

The optical density at 450 nm (OD 450 nm) resulting from the HIV ELISA test from the cell culture supernatant is given on the ordinate. At an optical density >2.0, the culture supernatant was diluted and the indicated OD value was calculated from the dilution. The cut-off value represents the detection limit of the HIV antigen determination.

In the antisense RNA-expressing cell line SSHUT K3/1-SXK2 HIV replication is completely inhibited over a time period of 30 days. The other transfected cell line shows delayed HIV replication in comparison to the wild-type cell line (U937).

We claim:

1. An expression vector construct comprising a promoter gene sequence operably linked to a subgenomic gene fragment of HIV-1 proviral DNA in the 3'→5' orientation, said promoter gene sequence comprising (i) a murine metallothionein promoter gene sequence fused to a human cytomegalovirus IE promoter gene sequence or (ii) a human cytomegalovirus IE promoter gene sequence, and said subgenomic gene fragment being selected from the group consisting of HIV-1 proviral DNA fragments 7514→474, 5786→474, 2096→474, 3825→681, 5786→4158, 5746→4648, 2369→1635, 3227→3003, 2099→678, 3829→2099, 4647→4157, 4157→3830, 605→455, 670→440, 825→535, 6070→5800, 5640→5020, 5600→5040, 8690→8300, and 9160→8800.

2. The expression vector construct according to claim 1, which is vector construct pSXK2.

3. The expression vector construct according to claim 1, which is vector construct pSXK1.

4. Transfected cells in culture comprising one or more expression vector constructs according to claim 1.

* * * * *

UNITED STATES PATENT AND TRADEMARK OFFICE
CERTIFICATE OF CORRECTION

PATENT NO. : 5,583,035
DATED      : December 10, 1996
INVENTOR(S): Kretschmer, et al.

It is certified that error appears in the above-indentified patent and that said Letters Patent is hereby corrected as shown below:

Title Page    [56] References Cited:  Insert -- U.S. PATENT DOCUMENTS:
4,963,481   10/1991   deVillers et al...435/69.1
5,032,396    7/1991   Williams et al... 424/85.2
5,168,062   12/1992   Stinski et al... 435/240.2 --

Signed and Sealed this

Twenty-fourth Day of June, 1997

Attest:

BRUCE LEHMAN

Attesting Officer        Commissioner of Patents and Trademarks